US009174371B2

(12) United States Patent
Smith

(10) Patent No.: US 9,174,371 B2
(45) Date of Patent: Nov. 3, 2015

(54) METHOD AND APPARATUS FOR MOULDING CANNULAE

(75) Inventor: Trevor Smith, Shepparton (AU)

(73) Assignee: SSB TECHNOLOGY PTY LTD, Perth (AU)

(*) Notice: Subject to any disclaimer, the term of this patent is extended or adjusted under 35 U.S.C. 154(b) by 516 days.

(21) Appl. No.: 12/530,185

(22) PCT Filed: Mar. 6, 2008

(86) PCT No.: PCT/AU2008/000296
§ 371 (c)(1),
(2), (4) Date: Sep. 21, 2009

(87) PCT Pub. No.: WO2008/106728
PCT Pub. Date: Sep. 12, 2008

(65) Prior Publication Data
US 2010/0102490 A1 Apr. 29, 2010

(30) Foreign Application Priority Data
Mar. 7, 2007 (AU) ................ 2007901163

(51) Int. Cl.
B29C 49/06 (2006.01)
B29C 45/17 (2006.01)
A61M 5/158 (2006.01)
A61M 25/00 (2006.01)
B29L 31/00 (2006.01)

(52) U.S. Cl.
CPC ............ *B29C 45/1711* (2013.01); *A61M 5/158* (2013.01); *A61M 25/0009* (2013.01); *B29C 2045/1719* (2013.01); *B29C 2045/1724* (2013.01); *B29C 2045/1728* (2013.01); *B29L 2031/7542* (2013.01); *B29L 2031/7544* (2013.01)

(58) Field of Classification Search
None
See application file for complete search history.

(56) References Cited

U.S. PATENT DOCUMENTS

| | | | | |
|---|---|---|---|---|
| 4,830,812 A | * | 5/1989 | Kauer | 264/572 |
| 5,484,278 A | * | 1/1996 | Berdan | 425/533 |
| 5,620,639 A | | 4/1997 | Stevens et al. | |
| 6,630,086 B1 | * | 10/2003 | Goral et al. | 264/40.4 |
| 6,767,487 B2 | * | 7/2004 | Pearson | 264/40.4 |
| 6,779,998 B2 | | 8/2004 | Goral et al. | |

* cited by examiner

Primary Examiner — Monica Huson
(74) Attorney, Agent, or Firm — Procopio, Cory, Hargreaves & Savitch LLP; Noel C. Gillespie

(57) ABSTRACT

The present invention provides apparatus and methods for injection molding polymeric cannulae from liquid polymeric materials. The method includes injecting pressurized liquid polymer into a mold cavity and into an overflow and forming a conduit by forcing pressurized working fluid through the solidifying liquid polymer into the overflow. The invention provides a mold for fluid-assisted injection molding articles from polymeric materials, the mold comprising at least two parts defining a cavity having a conduit portion incorporating a needle portion; a channel for liquid polymer ingress; a channel for pressurized fluid ingress; and an overflow in communication with the conduit portion. The mold may incorporate a plurality of cavities. Preferably the volume of the overflow is equal to or greater than the volume of the conduit portion. Preferably the mold incorporates a separating means for separating the overflow from a cannula portion of an article formed in the mold.

13 Claims, 7 Drawing Sheets

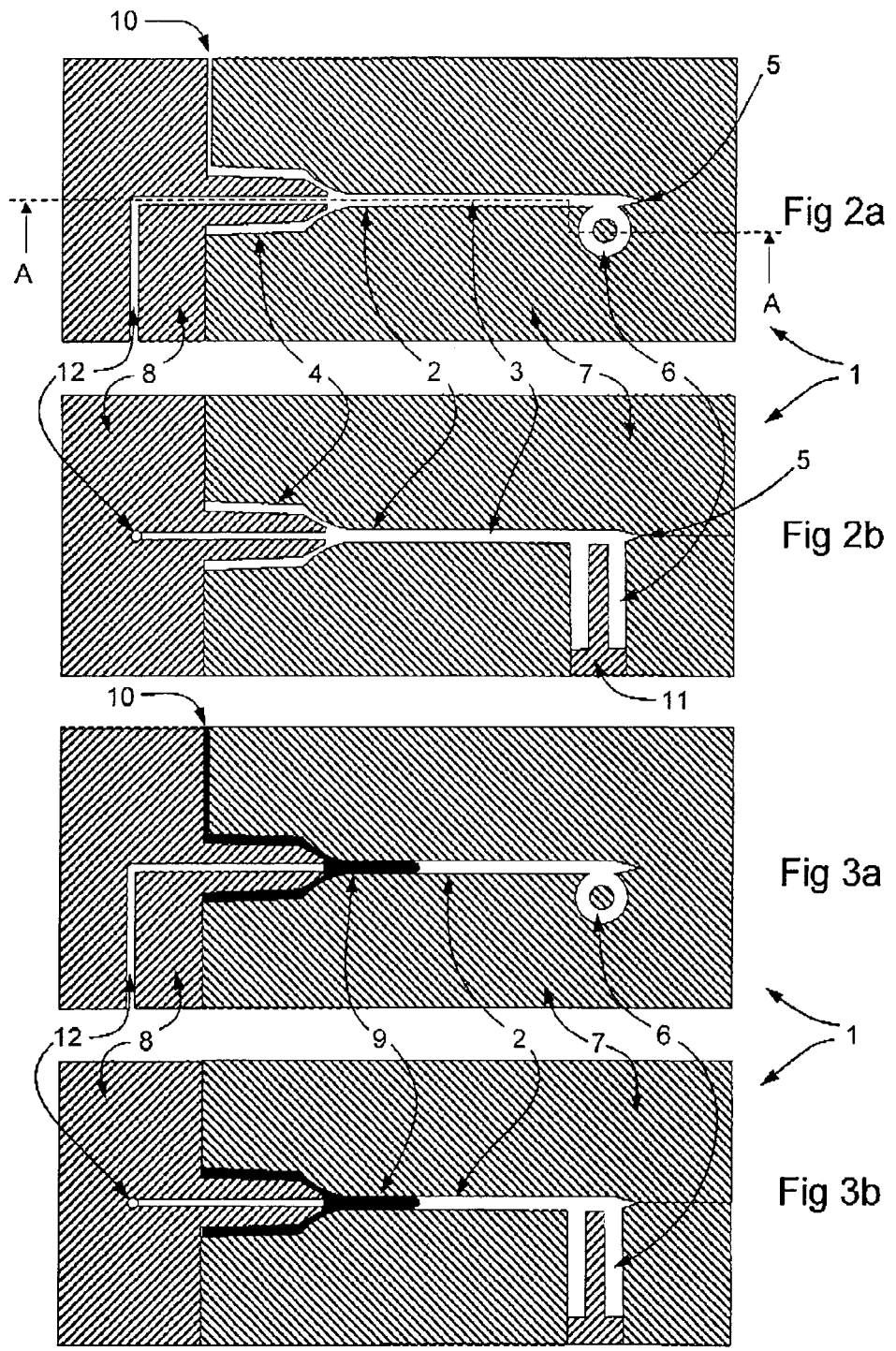

METHOD AND APPARATUS FOR MOULDING CANNULAE

CROSS REFERENCE TO RELATED APPLICATIONS

This application is a National Stage of International Application No. PCT/AU2008/000296, filed Mar. 6, 2008, claiming priority to Australian Patent Application No. 2007901163, filed Mar. 7, 2007, the contents of both applications being incorporated herein by reference in their entirety.

FIELD OF INVENTION

This invention relates to the field of manufacturing cannulae, in particular polymeric cannulae, and more particularly, methods and apparatus for fluid-assisted injection moulding of polymeric cannulae.

BACKGROUND TO THE INVENTION

It is known in the art that a cannula for use, particularly a single use, of transferring fluid into or from objects, in particular living beings, can be moulded from polymeric materials. Stevens, Smith and Bartlett described a method for manufacturing hypodermic needles in U.S. Pat. No. 5,620,639, hereinafter referred to as the '639 patent, which is incorporated herein by reference. The method disclosed in the '639 patent advantageously uses the properties of a liquid polymer and a working fluid for displacing liquid polymer from the interior of channel in a mould containing liquid polymer. The working fluid of the '639 patent is advantageously a gas that reliably creates an integrated "needle" comprising a cannula portion and a mounting hub portion for connection to a syringe, the cannula defining a conduit for passage of fluids between a reservoir and a subject. The mounting hub portion of a needle can take many forms, including being an extension of the needle portion. The cannula comprises of a conduit portion, a holding portion and a distal portion or entry portion, the cannula incorporating apertures known as ports for delivery of fluids. The holding portion may have the function of providing a means for holding the cannula as well as other functions such as, but not limited to, providing a reservoir for the fluid for delivery. While needles are cannulae that are characteristically used for transferring fluids in medical applications, there are many different types of articles that function as cannulae in many applications.

Methods for using fluid-assisted injection moulding of such small articles as cannulae rely on very precise metering of the volume of liquid polymer injected into the small constrained cavities required in the closed dies or moulds used for forming the articles. On the one hand, injecting too little volume of liquid polymer, for example, can result in an incomplete article. On the other hand, injecting too much volume of liquid polymer may lead to the working fluid not displacing enough of the liquid interior portion of the polymer to form a continuous conduit in the cannula. In either example, the formed article may be unsuitable for its intended use and must be discarded because it does not meet performance specifications, particularly in medical applications.

The method of the '639 patent has been shown to be effective using a single shot of liquid polymer in a mould containing a small number of cavities, say, 4 to 8, to each cavity producing a cannula in each cavity. However, large scale production of cannulae is necessary to be cost-effective and cheap relative to other methods of producing cannulae known in the art. Ideally, a mould for injection moulding of cannulae includes many cavities, each formed in the desired shape of a cannula so that a single cycle of injection (a single shot) of liquid polymer into the mould will produce many correctly formed cannulae, each meeting performance specifications. Other methods of injection moulding of cannulae are known, such as that taught in U.S. Pat. No. 6,767,496. All methods have shortcomings in controlling the flow of polymer.

A convenient way to produce many cannulae from a single shot is to inject the liquid polymer at a central feed point of a mould, which is in fluid communication with multiple runner feeds, each runner feeding to one of a series of cavities, each cavity having the shape of a cannula. It is known in the art that a slight excess of liquid polymer can be injected to a cavity, the excess material being allowed to exit the cavity at an overflow, the overflow sometimes called a "spillover" that is open to the atmosphere or presents very little resistance to flow.

Liquid polymers have very high viscosities. Very high pressures are required for injection moulding and, in fluid-assisted injection moulding of polymers, the working fluid must also be forced under high pressure into the mould for it to achieve the desired result of pushing more liquid polymer through the solidified polymer layer and into the overflow until the pressurised working fluid itself enters the overflow to create a through-conduit. Characteristically, the highly pressurised working fluid on reaching such an overflow undergoes a rush in velocity as it passes out of the liquid polymer. This method is not suitable for multiple channels in a mould. If there are many cavities in a mould the sudden rush of pressurised working fluid out of the polymer can destroy the cannulae at the worst, or result in a large proportion of defective cannulae. This method could result in mechanical damage to surfaces of the cannulae, the damage being observable under microscopic observation. Such damage could cause contamination if loose microscopic material was accidentally delivered to a subject or collected from a fluid source.

To achieve the required specifications of many cannulae produced in a single moulding cycle using the methods of the prior art for fluid-assisted injection moulding, the shot size (the total amount of liquid polymer injected) must be matched with the total volume of all the cavities in the mould. For example, a general purpose hypodermic needle will require about 100 mg per cannula with a mounting hub. Therefore a mould with 32 cavities, would require a shot of about 3 g of liquid polymer plus the feed system that traps some material. Reliability of the process requires that the amount of liquid polymer injected into each cavity must be controlled to a few milligrams, and the variability in total volume of liquid polymer from one shot to the next should be less than 1% to ensure each cavity always receives a suitable amount of liquid polymer to ensure the best product quality. Such tight tolerances in the amount of liquid polymer delivered using the current methods means that it is difficult to achieve the desired product consistency.

What is needed is a method and apparatus for moulding cannulae, the method and apparatus having improved reliability in reproducing the fine details in the cavities in a mould, particularly near the distal portion of the cannula.

BRIEF DESCRIPTION OF THE DRAWINGS

FIG. 2a shows a first longitudinal section of a mould for fluid-assisted injection moulding of a cannula.

FIG. 2b shows a longitudinal section, taken perpendicular to the longitudinal section in FIG. 2a.

FIG. 3a shows in longitudinal section the early ingress of liquid polymer into the cavity.

FIG. 3b shows a longitudinal section, taken perpendicular to the longitudinal section in FIG. 3a.

FIG. 4b shows a longitudinal section, taken perpendicular to the longitudinal section in FIG. 4a.

FIG. 5b shows a longitudinal section, taken perpendicular to the longitudinal section in FIG. 5a.

FIG. 6b shows a longitudinal section, taken perpendicular to the longitudinal section in FIG. 6a.

FIG. 7b shows a longitudinal section, taken perpendicular to the longitudinal section in FIG. 7a.

FIG. 8b shows a longitudinal section, taken perpendicular to the longitudinal section in FIG. 8a.

SUMMARY OF THE INVENTION

It is an object of the present invention to provide apparatus and methods to improve the reliability and consistency of cannulae produced from a mould used for the production of many cannulae from a single cycle of fluid-assisted injection moulding.

In one aspect the invention provides a method for forming an article from liquid polymeric material, the method comprising the steps of injecting pressurised liquid polymer into the cavity of a mould having an overflow, filling the cavity and a portion of the overflow with liquid polymer; injecting pressurised fluid into the solidifying polymer to form a conduit in the polymer, the pressurised fluid forcing liquid polymer into the overflow, allowing the polymer to solidify, and removing the article from the mould. Preferably the method further comprises the step of forming a port in the conduit by removing the solidified polymer in the overflow before removing the article from the mould. Preferably the entry of the polymer into the overflow is constrained.

The method includes the use of any suitable polymer including polymers of varying viscosities depending on the application or use for which the cannula is intended. For example, suitable polymers may be from the class known as thermoplastic polymers or the class known as thermosetting polymers, and may include LCP for hypodermic needles and rubbers for catheters.

In another aspect, the invention provides a mould for fluid-assisted injection moulding of articles from polymeric materials, the mould comprising at least two parts defining a cavity having a conduit portion incorporating a needle portion; a channel for liquid polymer ingress; a channel for pressurised fluid ingress; and an overflow in communication with the conduit portion. The mould may incorporate a plurality of cavities. Preferably the volume of the overflow is equal to or greater than the volume of the conduit portion. Preferably the mould incorporates a separating means for separating the overflow from a cannula portion of an article formed in the mould. Preferably the separating means is a mechanical means. Preferably the mechanical means is a cutting means. More preferably the cutting means is a rotary knife.

DESCRIPTION OF THE INVENTION AND MOST PREFERRED EMBODIMENTS

The objects of the invention are best understood with reference to the embodiments described herein and with reference to the figures. It will be understood by those skilled in the art that the invention is not limited to the embodiments shown in the figures but includes embodiments not illustrated but within the scope of the claims appended hereto.

Figure 1:
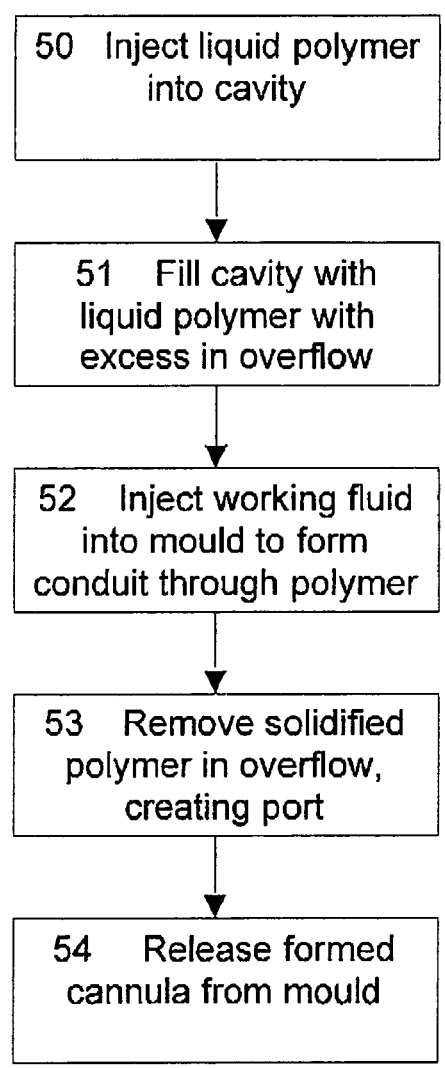
FIG. 1 shows the steps of fluid-assisted injection-moulding of liquid polymer to form a cannula with a lumen therethrough.
Figure 9A:
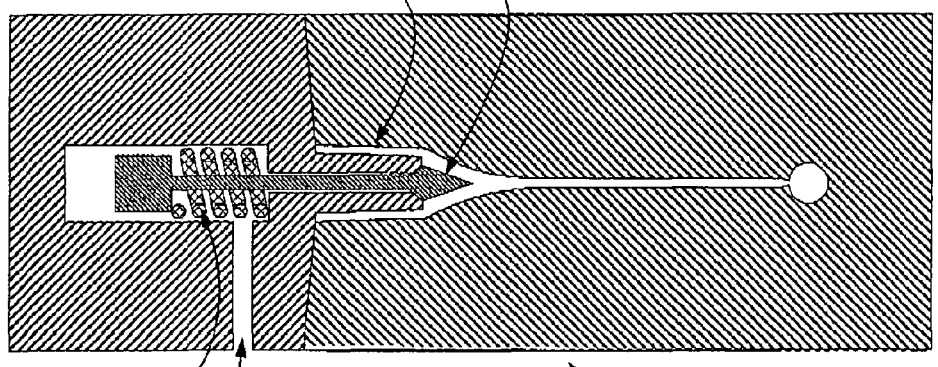
FIG. 9a and FIG. 9c show in longitudinal section a mould for forming a cannula having a pin valve and an overflow.
Figure 9B:
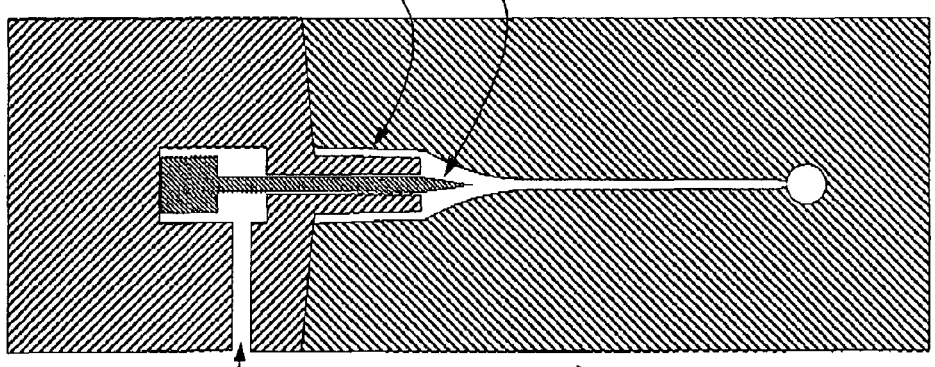
FIG. 9b shows in longitudinal section a mould for forming a cannula having a poppet valve and an overflow.

FIG. 1 is a schematic diagram illustrating the method of the invention. FIGS. 2 to 8 show one embodiment of the method and with suitable apparatus to practice the method. FIGS. 9 and 10 show alternative embodiments within the scope of the invention. FIG. 1 shows generally the steps comprising one aspect of the injection in which an article such as a cannula having a lumen therethrough is formed by fluid-assisted injection moulding. In a first step 50 an appropriate amount of liquid polymer is injected into at least one cavity in a mould which is ready to receive the liquid polymer. In a second step the at least one cavity is filled with adequate liquid polymer so that cavity is filled completely and excess material enters an overflow 51. In a third step working fluid is injected into the cavity 52, which forces an interior portion of the solidifying polymer into the overflow, thus creating a lumen. In a fourth step solidified polymer in the overflow is removed 53 at the interface between the overflow and cavity, conveniently creating a port continuous with the lumen of the conduit formed in the previous steps. In a final step 54 the cannula having at least one port is removed from the mould. The method is not restricted to moulding at least one cannula from at least one shot of liquid polymer, but includes moulding multiple cannulae from a shot of liquid polymer injected from a single source into a pathway continuous with several cannula-forming cavities. The method may also be used with multiple shots of liquid polymer into multiple pathways, each pathway feeding several cannula-forming cavities. Further, the at least one cannula may be formed from multiple shots of liquid polymer, including a first polymer and a second polymer and further polymers as the application requires. The polymer that is chosen may be selected from the class of polymers that are suitable for injection moulding. The method further includes engaging liquid polymer with other materials that may be placed into the mould.

FIGS. 2a and 2b show a mould 1 that may be used in performing the invention, the mould in longitudinal section, the mould (hatched) having parts 7, 8 that when positioned for operation, form a cavity 2 having a shape of an article with a conduit portion 3 in communication with a holding and entry portion 4 at a first end and a needle portion 5 at a second end. The mould also incorporates in the needle portion, and in communication with the conduit portion 3, an overflow portion 6. The mould includes a channel 10 for feeding liquid polymer 9 to the cavity 2. The mould also incorporates a channel 12 for ingress of pressurised working fluid for forming the hole or lumen the length of the cannula, creating a conduit for delivery of substances in a finished article.

FIG. 2a shows the empty mould 1 in position to receive liquid polymer in one orientation and FIG. 2b shows an alternative longitudinal section which is a stepped surface of the empty mould, taken along a stepped surface defined by the dashed line shown at A-A, the surface oriented at about a quarter turn or generally perpendicular to the orientation of the surface of the transverse longitudinal section of the empty mould of FIG. 2a. The orientation of FIG. 2b shows an alternative view of the overflow 6, showing a further portion 11 of the mould which incorporates mould material forming a central core of the overflow 6. The orientation of the mould in FIG. 2b also shows the pressurised working-fluid delivery-channel 12 as a circle because of the different perspective.

It will be understood that the relative proportions of the cavity volume 2 and overflow 6 shown in the figures are representative and not fixed. Preferably, the volume of the overflow approximates that of the volume of the cannula portion for large cannulae and many times the volume of the cannula portion for very fine needles.

FIGS. 3a and 3b shows the early ingress of liquid polymer 9 shown in black as it is injected into the cavity 2 of the mould shown in FIGS. 2a and 2b in a first step of the method of forming a fluid-assisted injection moulded article. As in FIG. 2, the perspectives of FIGS. 3a and 3b are that FIG. 3a is a longitudinal transverse section taken through the mould 1 of FIG. 2 and FIG. 3b incorporates a stepped surface defined by a similar line to A-A as shown in FIG. 2a. The liquid polymer 9 enters though an entry channel 10, the channel 10 formed between the faces of the first mould portion 7 and second mould portion 8. The channel 10 cannot be seen in FIG. 3b because of the change in orientation and perspective as described above.

Figure 4A:
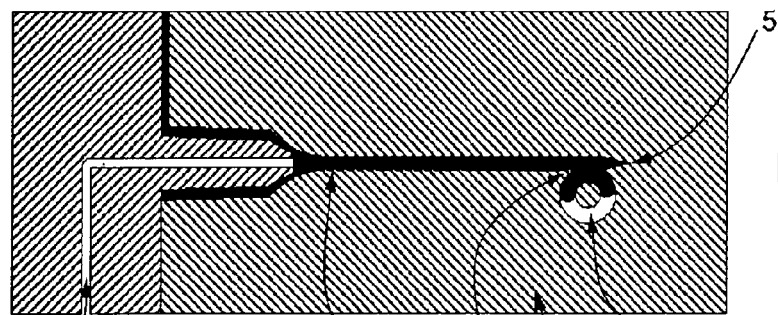
FIG. 4a shows in longitudinal section the finish of liquid polymer injection into the cavity and overflow.
Figure 4B:
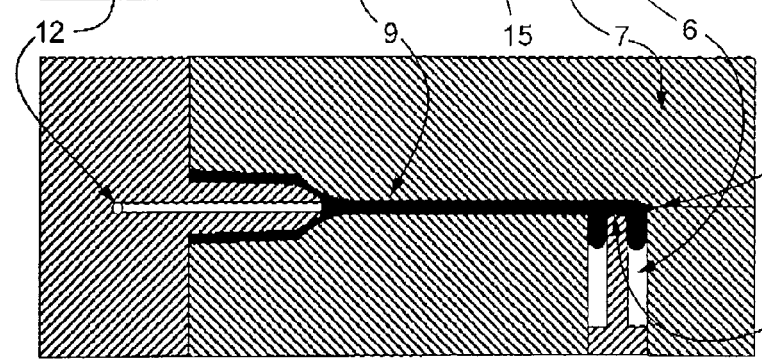

FIGS. 4a and 4b show the same sections of a mould as in FIGS. 2 and 3 but at a later step of the formation of the article wherein the liquid polymer 9 fills the cavity 2 completely and also fills some of the overflow 6. The overflow may take any suitable shape, including the cylinder as shown in the accompanying representations, but also, for example, as a tab (rectangular) shape. It will be understood that the liquid polymer as shown in FIG. 4b filling the overflow 6 is a continuous material within the overflow.

Figure 5A:
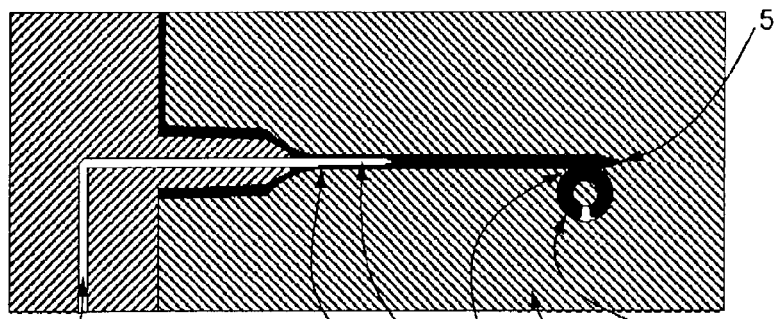
FIG. 5a shows in longitudinal section the progress of fluid injected into the mould pushing liquid polymer further into the cavity and overflow.
Figure 5B:
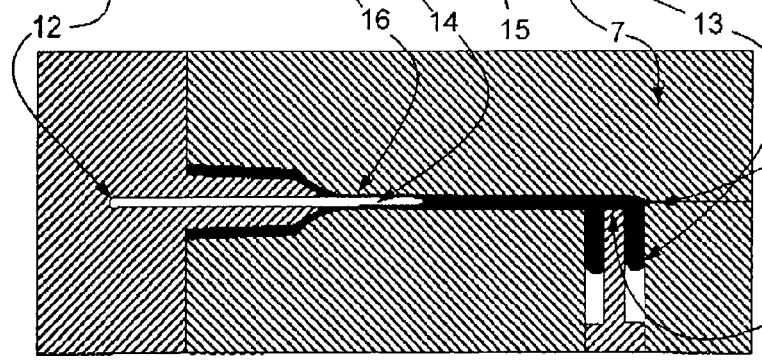
Figure 6A:
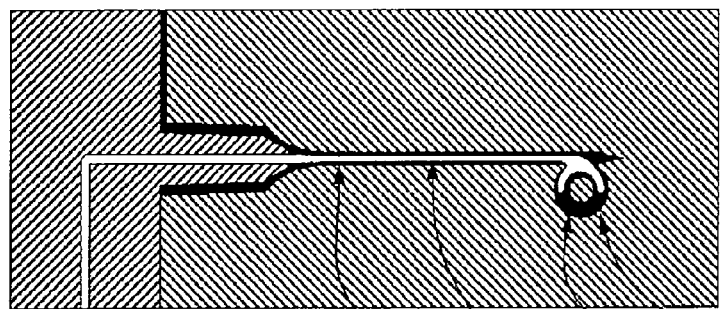
FIG. 6a shows in longitudinal section the after the working fluid has displaced enough liquid polymer to both fill the overflow and allow the working fluid to enter the overflow to create a cavity with a polymer conduit portion therethrough.

FIGS. 6a and 5b show a further step of the method of the invention wherein working fluid has been forced through the fluid channel 12 into the solidifying liquid polymer 16 to form the lumen 14 of cannula portion and conduit 3 continuous with the overflow 6 leaving a mass of liquid polymer 13 in the overflow. The channel forming the lumen 14 of the conduit with the working fluid forces the liquid polymer 9 into the overflow 6, entering the overflow 6 at a point 15 behind the distal portion 5 of the cannula.

Figure 6B:
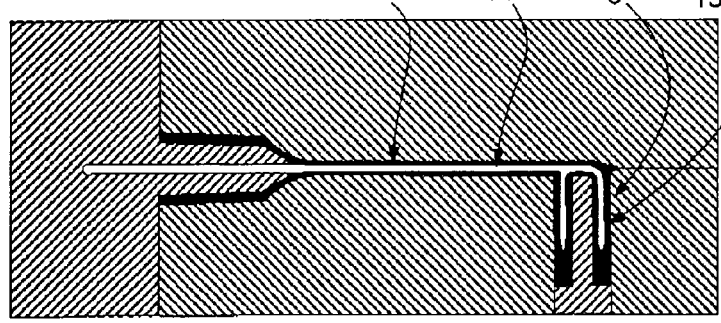

FIGS. 6a and 6b show in the same orientation to FIGS. 2 to 5, a transverse longitudinal section (FIG. 6a) and a surface approximately one-quarter turn, or perpendicular, perspective (FIG. 6b compared to FIG. 6a) of a further step of the method of forming an article using fluid-assisted injection moulding of polymers. At this stage the lumen 14 is continuous and forms a conduit 3 of solidified polymer 16 through the length of the cavity, the conduit not extending into the distal portion 5 of the needle. The lumen is also continuous with the overflow 6. A solidified mass of polymer 13 remains in the overflow and is continuous with the solidified polymer 16 of the conduit 3.

Figure 7A:
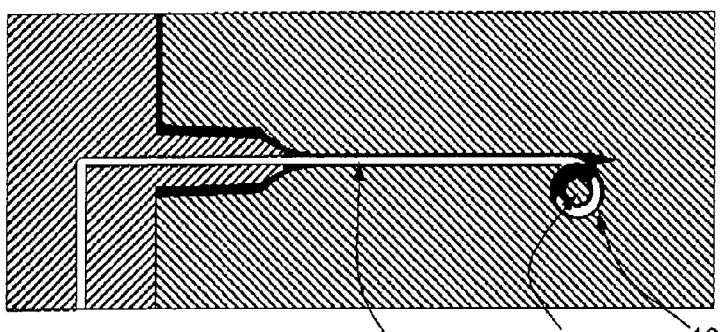
FIG. 7a shows in longitudinal section the polymer in the overflow being cut or separated from the polymeric conduit portion and forming the aperture or port.
Figure 7B:
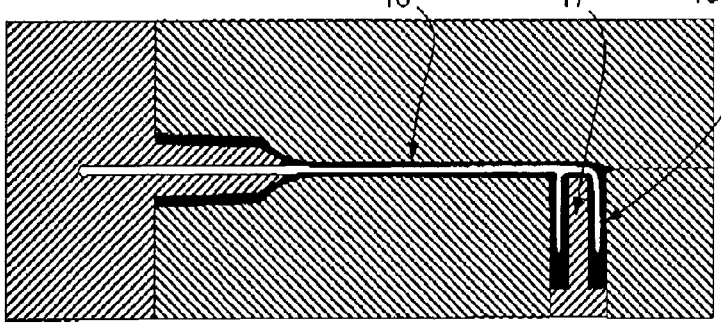
Figure 8A:
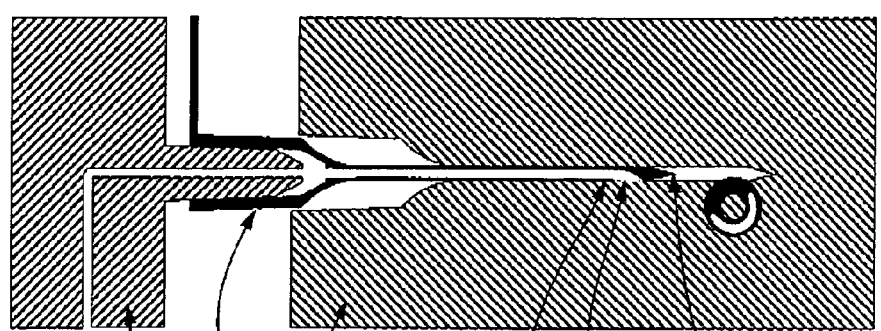
FIG. 8a shows in longitudinal section the disengagement of the parts of a mould to eject a fully formed polymeric cannula.
Figure 8B:
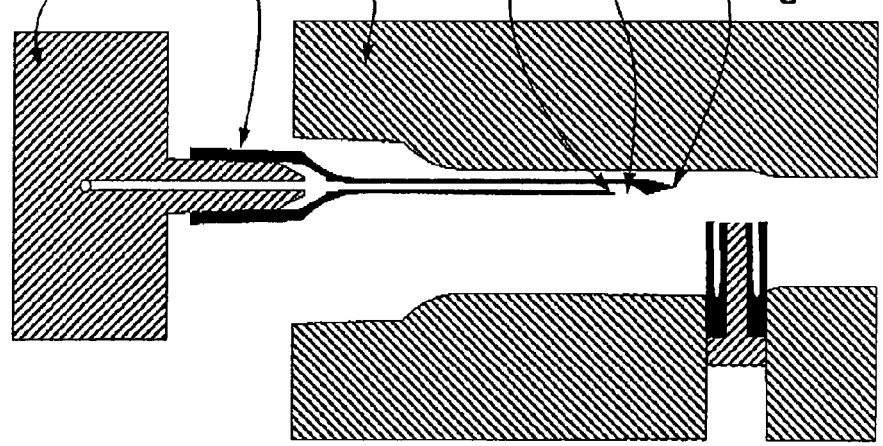

The method includes removing the formed article from the mould at this stage. Preferably the mass of solidified polymer 13 is separated from the conduit 3 in a further step before the article is removed from the mould. After it has solidified, excess polymer 13 in the overflow portion 6 can be separated conveniently with a suitable means 17 as shown in FIGS. 7a and 7b. The separation of the solidified polymer from the conduit forms an aperture or port 18 in the conduit 3 behind the needle portion 5 of the cannula. Preferably, the means is a mechanical means. Preferably the mechanical means is a rotary knife. Preferably the separation means is disposed in the mould. The method advantageously provides a smoother, cleaner surface at the aperture 18 of the annulus 19 (the port) than previous methods known in the art.

In the last step of the method the article is separated from the mould. The first 7 and second 8 mould portions are moved apart after the liquid polymer has solidified into a unitary article comprised of solidified polymer 16. A portion of the solidified polymer 13 may remain in the overflow portion of the mould where the separating means 17 is not included in the mould 1 until removed by ejection or other step.

In the method of the invention a cavity forming a cannula 1 is filled with liquid polymer 9. The cavity includes an overflow 6 that is enclosed and adjacent to the cannula. The invention includes a method and apparatus with more than one overflow for multiple ports in a single cavity, including side ports. The liquid polymer is injected into the cannula and through the conduit portion 3 and out into the overflow 6 so that the overflow is initially partially filled with liquid polymer 9. Entry of pressurised working fluid 11 into the mould 1 displaces any liquid polymer 9 in the conduit portion through a solidified polymer layer to fill the overflow. The incorporation of an overflow that is enclosed and constricted advantageously controls the reliability and reproducibility of formation of the lumen through the cannula in multiple cavities in a single mould and between sequential injections in the same cavity. The overflow preferably has a volume similar to, but may be much greater than, the volume of the conduit portion, which assists to reliably fill the entire conduit portion yet leave a reliable amount of space for the working fluid to displace liquid polymer without escaping the mould so that all cavities form a consistent annulus through the needle. The overflow thereby provides better tolerance for variations in volume of liquid polymer. Injection of pressurised working fluid into the mould, after the liquid polymer has been injected, forces the liquid polymer through a solidified layer of polymer in contact with the mould and into the overflow and in doing so forms an annulus through the cannula.

The shape of the overflow should provide resistance to the flow of liquid polymer to provide sufficient pressure drop to "pack out" fine details in the distal portion of the cannula such as a needle point. The preferred shape is a cylindrical overflow with a core pin up the centre so that it is forms a long thin "collar" of polymer connected to or near the end of the cannula. The thinness provides flow resistance comparable to that along the conduit portion to allow a build up in pressure to "pack out" fine details near the end of the cannula and distal portion. The length provides some tolerance for variations in volume of liquid polymer whilst maintaining flow resistance. The diameter of the "collar" can be many times larger than the cannula diameter to give a substantial volume relative to the conduit portion required for tolerance to process variations. A rotary knife in the mould then can cut the overflow like an "ice cream scoop", which avoids shearing the overflow. Since the overflow needs to be separated from the cannula, the interconnection should be thin and notched so that when cut, the cut is close, clean and reliable as possible.

The split lines or at least join lines in the mould should be placed at sharp edges or points of the distal portion of the cannula if required to produce, for example, a hypodermic needle. A split line is where the mould opens and closes. A join line is where two parts of the mould can come apart but stay in contact during production. Liquid polymer advantageously can penetrate the very restricted spaces created near these lines to form very sharp edges and points.

The method is most advantageously self-regulating. The very small volume of working fluid delivered to each cavity does not need to be set in advance or prescribed. Instead, under a particular, constant high pressure, each cavity receives the necessary working fluid to finish filling each overflow. That is, the surprising advantages of the method include that, firstly, while the volume of liquid polymer that is supplied with precision, the working fluid only displaces the necessary and sufficient amount of liquid polymer to fill overflows, and, secondly, that the working fluid will perform this function irrespectively of the variations in volume of liquid polymer among the cavities and among successive shots.

Most preferably, the method also includes that the overflows are constricted to provide continued and significant flow resistance throughout injection of polymer and working fluid to produce and maintain sufficient pressure upstream near ports and throughout the distal portion to 'pack out' final details in the cavity such as points and edges. The pressure gradient in the overflow should be comparable to the conduit portion.

Preferably, the mould incorporates a valve for each cavity to guide and control the entry of working fluid into the cavity. Preferably, the method includes using a valve to assist with the control of delivery of liquid polymer and pressurised fluid into the cavity. Examples of valves are shown in FIGS. 9a and 9b. In FIG. 9b, the hub-forming portion 20 of the mould 1 includes a pin valve 21. Alternatively, the hub-forming portion may include a poppet pin 22 as shown in FIG. 9a. Preferably, the pins are biased in position with a biasing means 23. Preferably, the biasing means is a spring as shown in FIGS. 9a and 9b. The preferred spring-loaded poppet pin means conveniently allows the orientation of the working fluid channel 12 to be located at either the side 24 or end 25 of the mould 1.

In embodiments incorporating poppet valves, the inlets 12 having poppet pins necessarily have to extend into the cannulae. For cannulae with small inlets of a comparable size to the outlets (ports) the poppet could operate in a cavity that is connected at the end or adjacent to the cannula and be subsequently trimmed from the cannula in a similar fashion to the overflow to create a conduit therethrough. As an example, FIG. 10 shows a double-ended needle that could be created with, for example, a single port at both ends. The inlet comprises of a cylindrical cavity with a poppet pin first filling then feeding the cannula. Conceptually, this is the equivalent arrangement as in FIGS. 2 to 9, but with trimming of the inlet as well as the outlet.

In practicing the method of the invention, working fluid under pressure will flow around the outside of the poppet pin 22, break through the layer of solidified polymer over the poppet pin and enter the liquid polymer. Once inside the solidified polymer layer, the working fluid will pressurise the liquid polymer while remaining within the solidified layer. The slight movement of the poppet pin also helps to create an entry for the working fluid. The timing and initial flow-rate of working fluid through the poppet are self-regulating. Since the injection pressure of the liquid polymer is much greater than the pressure of the working fluid, the working fluid can be pressurised at any time during polymer injection, which will last for a few tenths of a second, and the liquid polymer will not be able to penetrate the poppet gate. After the total metered shot of liquid polymer is delivered and its pressure decays to the same pressure as the working fluid shutoff by pressure from the polymer, the poppet pin will start to move forward to create an annular opening around the poppet pin to allow the already fully pressurised working fluid to gently enter the polymer with a steady flow-rate determined by the resistance to push more liquid polymer thought the conduit portion and into the overflow. There is no rush of high pressure working fluid into de-pressurised polymer to damage the entry portion of the cannula nor are there any timing difficulties associated with mechanically actuating a gate at just the right time relative to polymer injection and accurate to hundredths of seconds—too fast and polymer will enter the gate, too slow and the solidified polymer layer in the conduit portion has grown too thick.

Figure 9C:
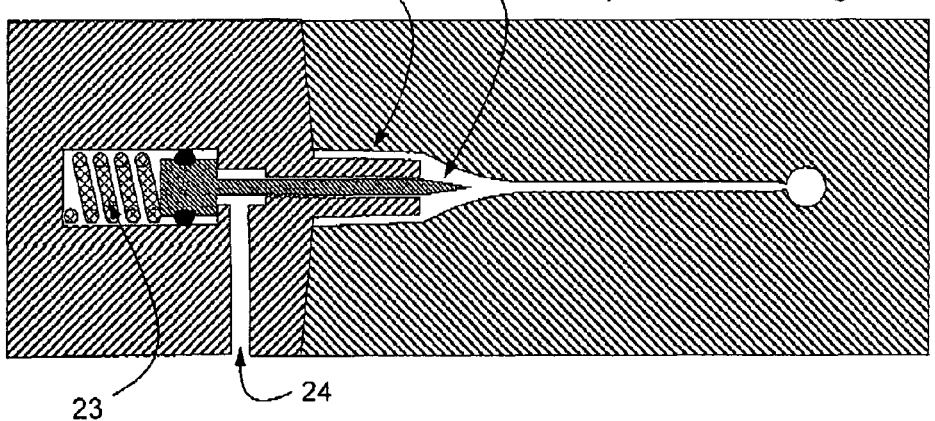
Figure 10:
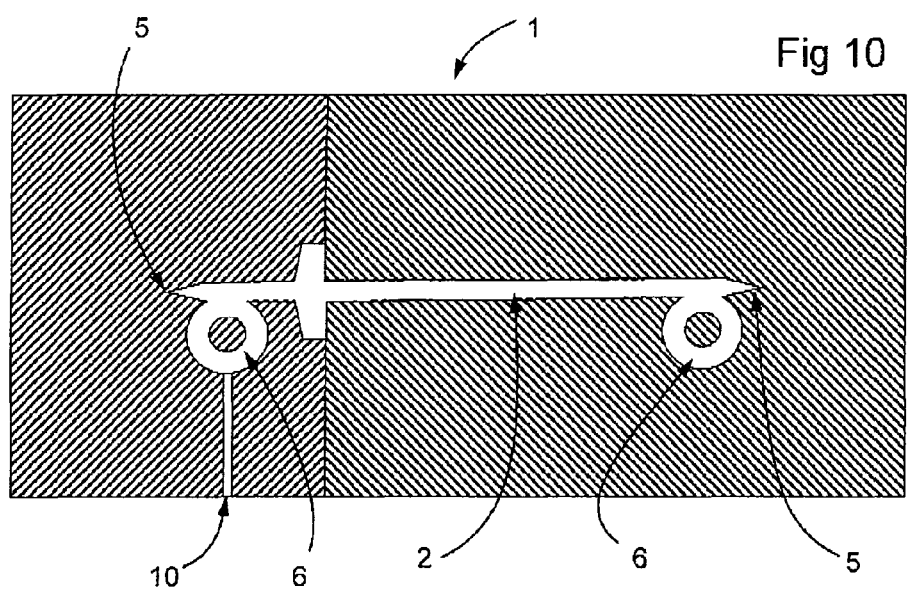
FIG. 10 shows a mould for a double-ended needle having ports at either end.

Alternatively, the formation of such an annular entry can be done with a pin 22 as illustrated in FIGS. 9b and 9c provided the clearance is small enough restrict polymer penetrating the entry. FIG. 9b shows an arrangement where the pin remains stationary. FIG. 9c shows an arrangement where the pin 22 moves backwards upon pressurisation of the working fluid. In another embodiment, the pin could be made to move forward if placed in a similar arrangement to that shown in FIG. 9a. Backwards moving pins are suitable to practise the invention but they would not have the same advantages of self-regulation because the movement must be actuated by the pressurisation of working fluid. Both forward-moving pins and stationary pins are self-regulating but may not help to create an entry for working fluid though the solidified polymer layer as much as effected by the poppet pin 22 in the embodiment shown in FIG. 9a.

The invention claimed is:

1. A mould for fluid-assisted injection moulding of polymeric materials, the mould comprising at least two parts defining a cavity having:
    a conduit portion incorporating a needle portion;
    a channel for liquid polymer ingress;
    a channel for pressurised fluid ingress; and
    a defined overflow in communication with the conduit portion, wherein the overflow is spaced upstream from a tip of the needle portion.

2. The mould as claimed in claim 1 further incorporating a plurality of cavities.

3. The mould according to claim 1, wherein the volume of the defined overflow portion is equal to or greater than the volume of the conduit portion.

4. The mould according to claim 1, further incorporating a separating means for separating the defined overflow portion from a cannula portion of an article formed in the mould.

5. The mould according to claim 4 wherein the separating means is a mechanical means.

6. The mould according to claim 5 wherein the mechanical means is a cutting means.

7. The mould according to claim 6 where the cutting means is a rotary knife.

8. The mould according to claim 2, wherein the volume of the defined overflow portion is equal to or greater than the volume of the conduit portion.

9. The mould according to claim 2, further incorporating a separating means for separating an overflow portion from a cannula portion of an article formed in the mould.

10. The mould according to claim 3, further incorporating a separating means for separating the defined overflow portion from a cannula portion of an article formed in the mould.

11. A method for forming an article from liquid polymeric material, the method comprising the steps of:

injecting pressurised liquid polymer into the cavity of a mould having a defined overflow, wherein the overflow is spaced upstream from a tip of a needle portion;

filling the cavity and a portion of the defined overflow with liquid polymer;

injecting pressurised fluid into the solidifying polymer to form a conduit in the polymer, the pressurised fluid forcing liquid polymer into the defined overflow;

allowing the polymer to solidify; and removing the article from the mould.

12. The method of claim 11 further comprising the step of forming a port in the conduit by removing the solidified polymer in the defined overflow before removing the article from the mould.

13. The method according to claim 11, wherein the entry of the polymer into the defined overflow is constrained.

* * * * *